(12) United States Patent
Baldacci et al.

(10) Patent No.: US 8,987,503 B2
(45) Date of Patent: Mar. 24, 2015

(54) PROCESS FOR THE SYNTHESIS OF AMINAPHTONE

(71) Applicant: Laboratori Baldacci SpA, Pisa (IT)

(72) Inventors: Massimo Baldacci, Pisa (IT); Marinella Roberti, Bologna (IT)

(73) Assignee: Laboratori Baldacci SpA, Pisa (PI) (IT)

( * ) Notice: Subject to any disclaimer, the term of this patent is extended or adjusted under 35 U.S.C. 154(b) by 0 days.

(21) Appl. No.: 14/263,911

(22) Filed: Apr. 28, 2014

(65) Prior Publication Data

US 2014/0323747 A1    Oct. 30, 2014

(30) Foreign Application Priority Data

Apr. 30, 2013  (IT) ............... MI2013A0703

(51) Int. Cl.
  C07C 69/76    (2006.01)
  C07C 227/02   (2006.01)
  C07C 229/66   (2006.01)
  C07D 303/12   (2006.01)

(52) U.S. Cl.
  CPC ............. *C07C 227/02* (2013.01); *C07C 229/66* (2013.01); *C07D 303/12* (2013.01)
  USPC ........................................................ 560/128

(58) Field of Classification Search
  CPC .................................................. C07C 227/02
  USPC ........................................................ 560/128
  See application file for complete search history.

(56) References Cited

U.S. PATENT DOCUMENTS 3,639,432 A    2/1972  Berti

FOREIGN PATENT DOCUMENTS

EP    2 390 246 A1    11/2011

OTHER PUBLICATIONS

Castelli, et al.; "Treatment with Aminaftone in the complex chronic venous insufficiency"; Phlebolymphology; vol. 1, pp. 241-244; 1988. (with English Abstract).
Gelso, et al.; "Eziopatogenesi dell'insufficienza Venosa Cronica: Attualita dell'Aminaftone (Capillarema) nelle Alterazioni del Microcircolo"; Farmaci & Terapia, International Journal on Drugs and Therapy; vol. 21, No. 1-2, pp. 1-8; 2004. (with English Abstract).
Italian Search Report of Italian Application No. ITMI20130703 with a mailing date of Jan. 22, 2014.
Scorza, et al.; "Aminaftone, a Derivative of 4-Aminobenzoic Acid, Downregulates Endothelin-1 Production in ECV304 Cells"; Drugs R D; vol. 9, No. 4, pp. 251-257 (2008).
Scorza, et al.; "Effects of Aminaftone 75 mg TID on Soluble Adhesion Molecules: A 12-Week, Randomized, Open-Label Pilot Study in Patients with Systemic Sclerosis"; Clinical Therapeutics; vol. 30, No. 5, pp. 924-929 (May 2008).
Villaverde, et al.; "Vascular Permeability Modification by Aminaftone"; Review of Clinical and Experimental Pharmacology; vol. 6, No. 1, pp. 9-14; 1989. (with English Abstract).
Xiao, et al.; "1,4-Naphthoquinone Cations as Antiplasmodial Agents: Hydroxy-, Acyloxy-, and Alkoxy-Substituted Analogues"; ACS Medicinal Chemistry Letters; vol. 3, pp. 1029-1033 (2012).
Zambelli, et al.; "Efficacy of aminaftone in a rat model of monocrotaline-induced pulmonary hypertension"; European Journal of Pharmacology; vol. 667, pp. 287-291 (2011).

*Primary Examiner* — Taofiq A Solola
(74) *Attorney, Agent, or Firm* — Perkins Coie LLP; Viola T. Kung

(57) ABSTRACT

The present invention concerns a new process for the synthesis of aminaphtone, which makes use of non-toxic solvents and reagents, under mild reaction and temperature conditions. The aminaphtone obtained with the method of the present invention also has a purity of at least 98% in weight. The method comprises the following steps: a) epoxidating menadione 1 to provide epoxide 2, b) acidifying epoxide 2 to provide hydroxynaphthoquinone 3, c) esterifying between hydroxynaphthoquinone 3 and 4-aminobenzoyl chloride to obtain compound 4, and d) reducing compound 4 in the presence of a reducing agent in water to obtain aminaphtone.

17 Claims, No Drawings

PROCESS FOR THE SYNTHESIS OF AMINAPHTONE

This application claims the priority of Italian patent application No. MI2013A000703, filed on Apr. 30,2013; the contents of the above-identified application is incorporated herein by reference in its entirety.

FIELD OF THE INVENTION

The present invention concerns a new process for the synthesis of aminaphtone, which adopts non-toxic solvents and reagents, under mild reaction and temperature conditions.

BACKGROUND

Capillary fragility is a very common problem, in particular among the female population. The intake of anticoagulant drugs, infections, deficiency of certain vitamins and heredity can result in decreased capillary resistance.

The therapeutic use of aminaphtone (2-hydroxy-3-methyl-4-naphthohydroquinone-2-p-aminobenzoate) as vasoprotective drug has been known for many years.

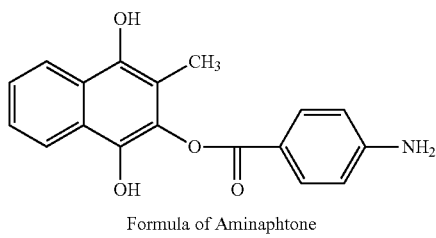 [SMILES: Cc1c(OC(=O)c2ccc(N)cc2)c(O)c2ccccc2c1O]

Formula of Aminaphtone

Studies published in scientific literature show its effectiveness as a modulator/normaliser of capillaries in particular pathological conditions (see references 1, 2 and 3).

More recent studies have revealed that aminaphtone is also effective against disorders related to an endothelial damage of the arteriovenous microcirculation. Aminaphtone in fact inhibits the synthesis of endogenous substances responsible for the endothelial damage such as E-selectin, and endothelin-1, thereby highlighting its essential role in the prevention and treatment of various inflammatory diseases of the microcirculation (see references 4 and 5).

In addition, as regards pulmonary hypertension, experimentally induced in rats by the administration of monocrotaline, the effectiveness of aminaphtone was highlighted concerning various parameters investigated, such as the reduction of the plasma concentration of endothelin and of the hypertrophy of the right heart and the reduction in thickness of the pulmonary arteries (see reference 6).

The synthesis of aminaphtone was first described in U.S. Pat. No. 3,639,432.

The last two steps of the multi-step synthesis provides firstly the formation of an ester bond between 2-hydroxy-3-methyl-1,4-naphthohydroquinone and one p-nitrobenzoyl halide in benzene, and subsequently the catalytic hydrogenation in dioxane under pressure, to obtain the final product. This preparation is shown in Scheme 1 below.

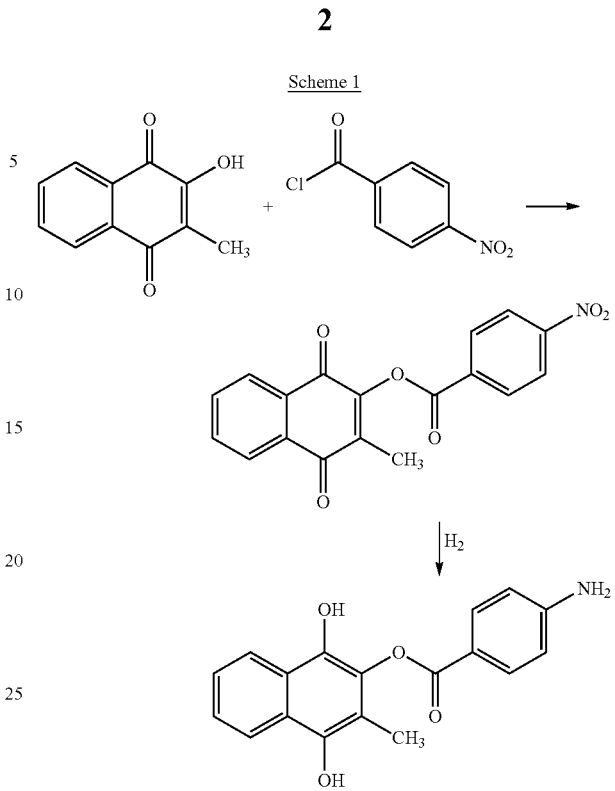

Scheme 1

The use of toxic solvents and drastic conditions make this preparation method poorly suitable for an industrial scale. Furthermore, the aminaphtone obtained through this process, has a degree of purity that is unsuitable for use as a drug. In fact, an impurity rapidly forms alongside the aminaphtone, that corresponds to an over-oxidation product with the following formula:

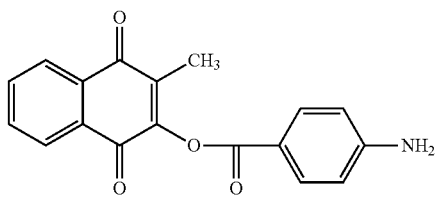 [SMILES: CC1=C(OC(=O)c2ccc(N)cc2)C(=O)c2ccccc2C1=O]

Recently a new method for the synthesis of aminaphtone was described in the European patent application EP2390246A1.

The above European patent application discloses that it is possible to obtain the aminaphtone with high purity by reaction of 2-hydroxy-3-methyl-1,4-naphthohydroquinone and p-nitrobenzoyl chloride in toluene, and subsequent catalytic hydrogenation in dioxolane under reduced pressure, in the presence of a metal catalyst.

This synthesis despite being more advantageous than U.S. Pat. No. 3,639,432, continues to make use of toxic substances such as pyridine; traces of palladium on carbon may also be present in the production batches, thus preventing its use in the pharmaceutical field.

Therefore, there is still the need to develop a new process for the synthesis of aminaphtone that does not make use of toxic substances, and makes it possible to obtain a final product with a high degree of purity, without having to resort to numerous purification steps.

REFERENCES

1. Gelso E, Corradetti R. Eziopatogenesi dell'insufficienza venosa cronica: attualitá dell'Aminaftone (Capillarema) nelle alterazioni del microcircolo. Farmaci e terapia, Vol XXI, 1/2, 35-42, 2004
2. Villaverde C. A. et al. Modificacion de la permeabilidad vascular con Aminaftone. Rev. Farmacol. Clin. Exp., 6, 9-14, 1989.
3. Castelli P. et al. Trattamento con Aminaftone nell'insufficienza venosa cronica complicata. Flebolinfologia 1, 241-244, 1988.
4. Scorza R et al. Effects of aminaftone 75 mg TID on soluble adhesion molecules: a 12-week, randomized, open-label pilot study in patients with systemic sclerosis. Clin Ther. 30, 924-929, 2008.
5. Scorza R et al. Aminaftone, a derivative of 4-aminobenzoic acid, downregulates Endothelin-1 production en ECV 304 cells. An in vitro study. Drugs R. D., 9, 251-257, 2008.
6. Zambelli V. et al. Efficacy of aminaftone in a rat model of monocrotaline-induced pulmonary hypertension. Eur J Pharmacol, 667(1-3), 287-91, 2011.

SUMMARY OF THE INVENTION

The present invention is directed to a process for the synthesis of aminaphtone. The process comprises the following steps: a) epoxidating menadione 1 to provide epoxide 2, b) acidifying epoxide 2 to provide hydroxynaphthoquinone 3, c) esterifying between hydroxynaphthoquinone 3 and 4-aminobenzoyl chloride to obtain compound 4, and d) reducing compound 4 in the presence of a reducing agent in water to obtain aminaphtone.

The present invention is also directed to aminaphtone having a purity of at least 98% in weight.

The present invention is further directed to Epoxide 2 and Compound 4.

The chemical structures of the above-identified compounds are shown in the application.

DETAILED DESCRIPTION OF THE INVENTION

With the present invention a process for the synthesis of aminaphtone has been found, suitable for production on an industrial scale, which provides the desired product with high purity, without the use of toxic solvents or reagents.

All the operations of the process of the present invention are suitable for production on a commercial scale and are carried out in mild reaction and temperature conditions.

According to the present invention "high purity" is understood to mean a purity higher than 95% in weight.

The present invention concerns the preparation of aminaphtone according to Scheme 2 below.

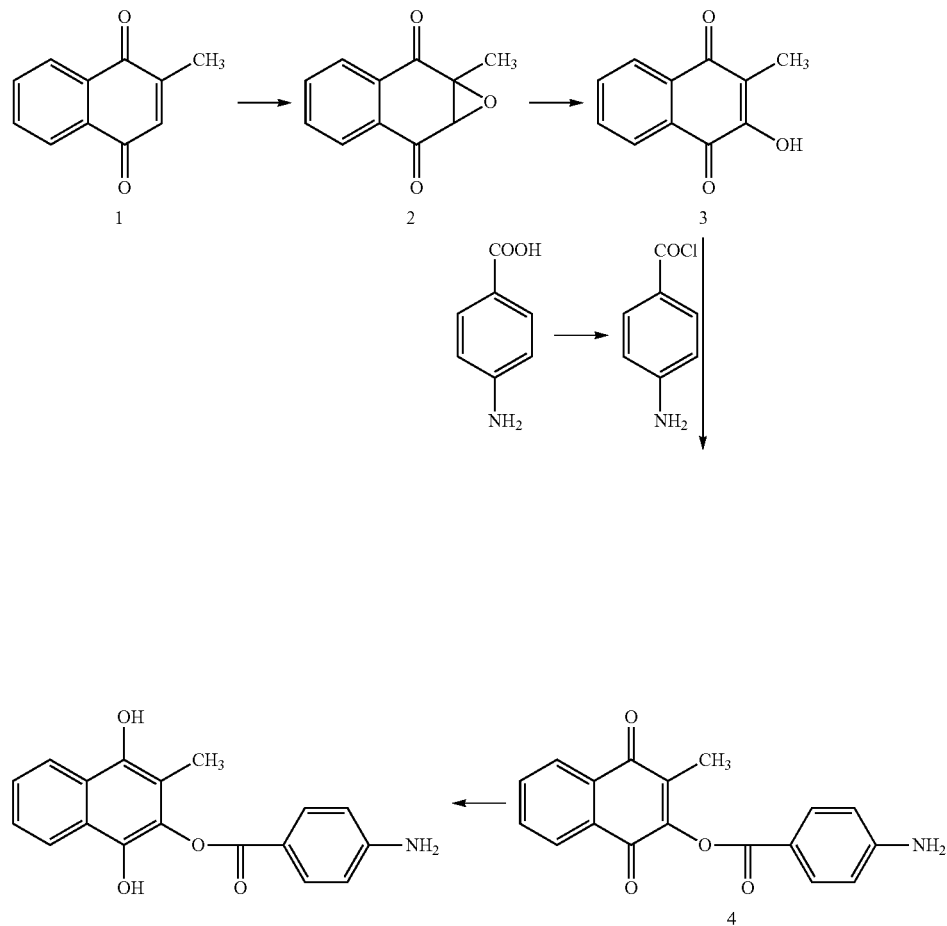

Scheme 2

According to the present invention, menadione 1, which is commercially available, is subjected to an epoxidation reaction using a peroxide, to provide the corresponding epoxide 2.

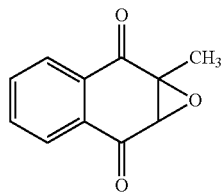

2

Preferably, said peroxide is hydrogen peroxide or a peroxycarboxylic acid selected from meta-chloroperoxybenzoic acid and peroxyacetic acid, and more preferably it is hydrogen peroxide.

According to an aspect of the present invention, the molar ratio between said peroxide and the menadione 1 is between 5:1 and 0.5:1, preferably between 2:1 and 1:1, and more preferably about 1.5:1.

According to the present invention, the epoxidation reaction is preferably carried out in the presence of a base, more preferably an inorganic base selected from alkali metal hydroxides, such as sodium hydroxide, potassium hydroxide, alkali metal carbonates, such as sodium carbonate, and potassium carbonate.

A particularly preferred base according the present invention is sodium hydroxide 2 M.

Preferably, said base is added to the reaction mixture in a molar ratio between 0.2:1 and 1.7:1, more preferably between 0.3:1 and 1:1, even more preferably it is about 0.5:1, with respect to menadione 1.

According to the present invention, said epoxidation reaction is conducted in a polar solvent selected from water and $C_1$-$C_4$ alkanols, or a mixture of these, preferably in a mixture of water and $C_1$-$C_4$ alkanols, more preferably in a mixture of water and methanol, in a volume ratio between 1:1 and 1:10, preferably between 1:2 and 1:6, more preferably about 1:4.

The reaction mixture is brought to a temperature between −20° C. and room temperature, preferably between −10° C. and 10° C., more preferably at about 0° C. and left under stirring for a time between 10 minutes and 2 hours, preferably between 20 minutes and 1 hour, more preferably for about 30 minutes.

According to an aspect of the present invention, the epoxide 2 is then opened in the presence of a strong acid, preferably an inorganic acid selected from hydrochloric acid, sulphuric acid, more preferably sulphuric acid 96%, to provide the corresponding hydroxynaphthoquinone 3.

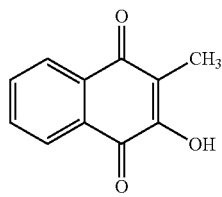

3

Preferably, said acid is used in a molar ratio between 2:1 and 10:1, more preferably between 4:1 and 8:1, even more preferably about 6:1, with respect to the hydroxynaphthoquinone 3.

The acid is added preferably at a temperature between 0° C. and 60° C., more preferably at room temperature and the reaction mixture is left under stirring for a time between 5 minutes and 30 minutes, preferably for about 15 minutes.

According to a further aspect of the present invention, the hydroxynaphthoquinone 3 is put to react with the chloride of 4-aminobenzoyl, of formula

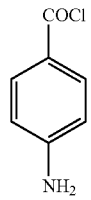

to provide the compound 4

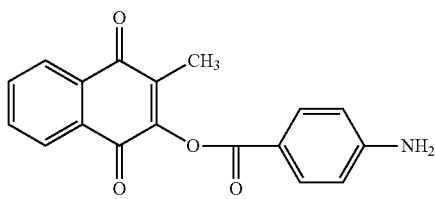

4

Preferably, the molar ratio between the chloride of 4-aminobenzoyl and hydroxynaphthoquinone 3 is between 0.8:1 and 2:1, more preferably between 1:1 and 1.75:1, even more preferably it is about 1.55:1.

According to an aspect of the present invention, said reaction takes place in a nonpolar organic solvent selected from aromatic hydrocarbons, such as toluene, chlorinated solvents, such as chloroform, methylene chloride, and ether solvents such as diethyl ether, diisopropyl ether, tetrahydrofuran, or a mixture thereof.

Preferably, said reaction is carried out in an ether solvent, more preferably in tetrahydrofuran.

According to the present invention, the esterification between the hydroxynaphthoquinone 3 and chloride of 4-aminobenzoyl is carried out at a temperature between −10° C. and room temperature, preferably at about 0° C.

Said condensation is preferably carried out in the presence of a base to remove the hydrochloric acid developed, more preferably in the presence of an organic base selected from triethylamine, N,N,N$^1$,N$^1$-tetramethylethylenediamine (TMEDA), 1,4-diazabicyclo[2.2.2]octane (DABCO), even more preferably in the presence of triethylamine.

According to the present invention, the molar ratio between said base and the hydroxynaphthoquinone 3 is between 0.7:1 and 1.5:1, preferably between 0.9:1 and 1.3:1, and more preferably about 1.1:1.

The 4-aminobenzoyl chloride can be obtained by techniques known to a person skilled in the art. Preferably it is obtained by chlorination of 4-aminobenzoic acid, in the presence of a chlorinating agent selected from thionyl chloride and oxalyl chloride.

A particularly preferred chlorinating agent, according to the present invention, is thionyl chloride.

The molar ratio of said chlorinating agent and the 4-aminobenzoic acid is between 1:1 and 20:1, preferably between 5:1 and 15:1, more preferably it is about 10:1.

The chlorination reaction can be performed in the presence or in the absence of a solvent, it is preferably carried out in the absence of a solvent, at a temperature between room temperature and the boiling temperature of the chlorinating agent, preferably between 50° C. and 60° C.

According to a further aspect of the present invention, the compound 4 is reacted with a reducing agent, in water to give the aminaphtone.

Suitable reducing agents according to the present invention are sulphites.

A preferred reducing agent according to the present invention is sodium hydrosulphite.

According to the present invention, the molar ratio between said reducing agent and the compound 4 is between 5:1 and 30:1, preferably between 10:1 and 20:1, and more preferably it is about 17:1.

Preferably, the aforementioned reduction reaction occurs at a temperature between room temperature and 100° C., more preferably between 40° C. and 80° C., and even more preferably at about 60° C.

A further aspect of the present invention is represented by the compounds:

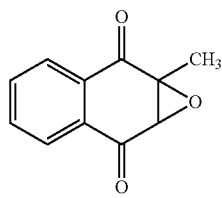

2

These are

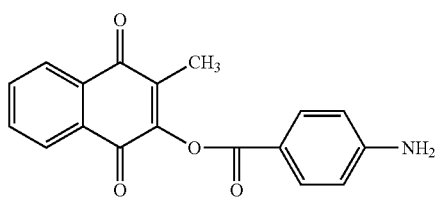

4 intermediate compounds obtained in the process of the present invention.

A further aim of the present invention is therefore the use of at least one of these compounds, that is of the epoxide 2 and/or of the compound 4, as an intermediate in the synthesis of the aminaphtone.

The aminaphtone, obtained according to the process of the present invention, has a purity of at least 98%. This high purity makes it particularly suitable for use as active ingredient in the preparation of a drug.

A further aim of the present invention is the aminaphtone that can be obtained by means of the process of the present invention.

The process of the present invention thus allows the preparation of the aminaphtone, with a high purity, using non-toxic solvents, mild reaction conditions, reduced reaction times, and a greater ease of handling of the reagents.

EXAMPLES

Synthesis Procedures

Example 1

Preparation of Menadione Epoxide (2) (1a-methyl naphtyl[2,3-b]oxyrene-2,7 (1Ah-7Ah)-dione)

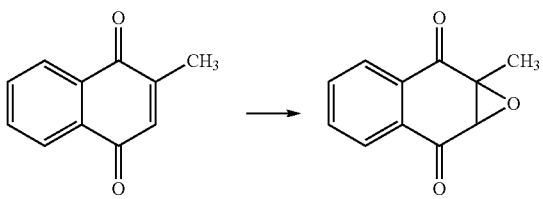

Menadione crystalline (1) (5 g, 29.04 mmol, 1 equivalent) and 2 M NaOH (7.26 mL, 14.52 mmol, 0.5 equivalents) are dissolved in a mixture of methanol/water 4:1 (50 mL) at 0-2° C. After stirring at this temperature for 10 minutes, 35% hydrogen peroxide is added (4.2 mL, 43.56 mmol, 1.5 equivalents). Work-up: after 30 minutes at 0° C. the product is extracted with ethyl ether. The organic phase is dried over $Na_2SO_4$ and evaporated under reduced pressure. A whitish powder is obtained (5 g, 26.57 mmol). Yield: 91.5%.

Example 2

Preparation of Menadione Epoxide (2)

The preparation method is identical to the one in example 1.

Work-up: The MeOH is evaporated from the reaction mixture, the product is filtered and left to dry. A whitish powder is obtained (5 g, 26.57 mmol). Yield: 91.5%.

Example 3

Preparation of 2-hydroxy-3-methyl-1,4-naphthohydroquinone (3)

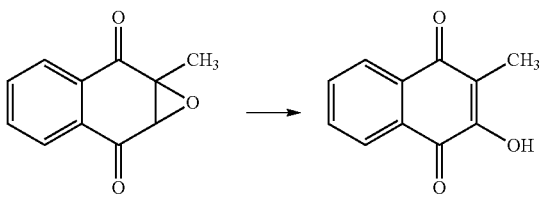

Menadione epoxide (2) (5 g, 26.5 mmol, 1 equivalent) is dissolved in 96% sulphuric acid (18 M, 8.8 mL, 159 mmol, 6 equivalents) to obtain a brilliant dark red solution. This is stirred at room temperature for 15 minutes. Work-up: water is added and the mixture is extracted with ethyl ether. The organic phases are combined, dried over $Na_2SO_4$ and filtered and the solvent is evaporated under reduced pressure. The product is washed with water. Yellow/green powder (4.5 g, 23.91 mmol). Yield: 83-93%.

Example 4

Preparation of 4-aminobenzoyl chloride

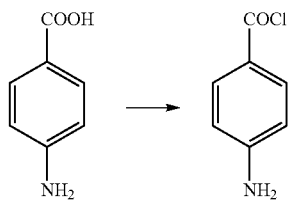

The 4-aminobenzoic acid (2.00 g, 14.58 mmol, 1 equivalent) is dissolved in thionyl chloride (10.59 mL, 145.8 mmol, 10 equivalents) under nitrogen atmosphere and the reaction is heated under weak reflux (T=50-60° C.) for about 2 hours, until the acid is completely converted into the corresponding acyl chloride.

The excess thionyl chloride is evaporated under reduced pressure. A pale yellow oil is obtained that at 0° C. becomes a yellow crystalline powder. As a result 2.26 g (14.58 mmol) of the desired product are obtained with a 100% yield. The product is used in the next step without purification.

Example 5

Preparation of 3-methyl-1,4-dioxol-1,4-dihydronaphthalen-2-yl-4-aminobenzoate (4)

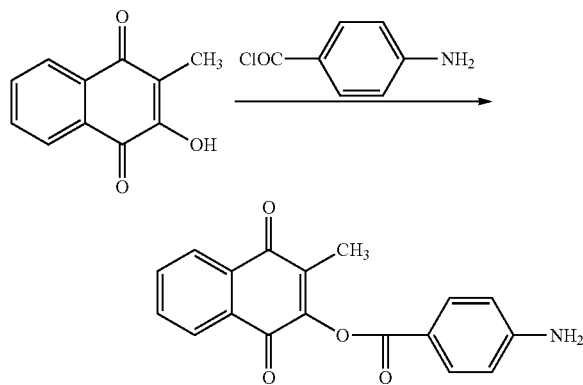

The compound (3) (2.27 g, 12.06 mmol, 1 equivalent) is added to a solution of $NEt_3$ (1.85 mL, 13.27 mmol, 1.1 equivalents) in 30 mL of dry THF, at room temperature and under nitrogen atmosphere. The chloride of 4-aminobenzoyl (2.90 g, 18.69 mmol, 1.55 equivalents) dissolved in 30 mL THF is then added at 0° C. and the mixture is left under stirring for 20 minutes at the said temperature.

Work-up: the reaction mixture is quenched with a phosphate buffer at pH 7.00 and the organic phase is extracted with $CH_2Cl_2$. The combined organic extracts are washed several times with the phosphate buffer at pH 7.00, then they are washed with brine, dried over $Na_2SO_4$ and concentrated under reduced pressure. An orange powder (3.55 g, 11.55 mmol) is obtained, corresponding to the desired product. Yield 96%.

Example 6

Preparation of the Aminaphtone

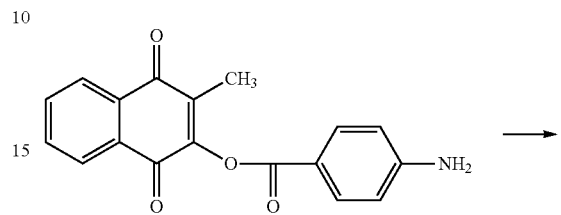

The product (4) (1 g, 3.25 mmol, 1 equivalent) is suspended in 100 mL of $H_2O$ in a steel reactor. It is saturated with nitrogen and a solution of sodium dithionite (9.62 g, 55.25 mmol, 17 equivalents) in 120 mL of $H_2O$ is added. It is then stirred vigorously, the reaction is heated to 60° C. and is left at this temperature for about half an hour. A whitish flocculent precipitate is obtained that is filtered to give a flesh pink powder (810 mg, 2.62 mmol) corresponding to the desired crude product. This product is suspended in a solution of sodium hydrosulphite (8%) and then washed with water until the sulphates are no longer present in the washing water. The final product (purity 98%) is recovered by drying at 50-70° C. after having been filtered. Final yield of the pure product: about 80%

What is claimed is:
1. A method for preparing aminaphtone, comprising the following steps:
   a) epoxidating menadione 1

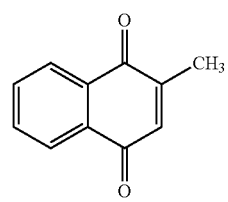

to provide epoxide 2

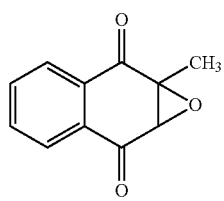

b) acidifying epoxide 2 to provide hydroxynaphthoquinone 3

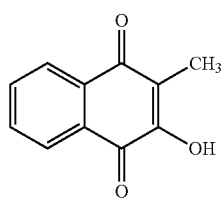

c) esterifying between hydroxynaphthoquinone 3 and the chloride of 4-aminobenzoyl of formula

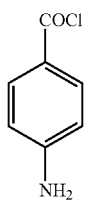

to obtain compound 4

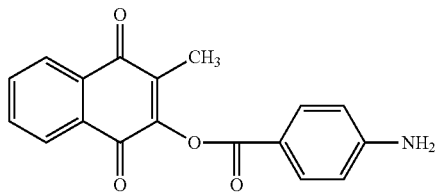

d) reducing compound 4 in the presence of a reducing agent in water to obtain aminaphtone.

2. The method according to claim 1, wherein said epoxidation reaction a) is carried out in the presence of a peroxide.

3. The method according to claim 2, wherein said peroxide is hydrogen peroxide or a peroxycarboxylic acid selected from the group consisting of meta-chloroperoxybenzoic acid and peroxyacetic acid.

4. The method according to claim 2, wherein the molar ratio between said peroxide and the menadione 1 is between 3:1 and 0.5:1.

5. The method according to claim 1, wherein the epoxidation reaction is carried out in the presence of a base.

6. The method according to claim 5, wherein said base is an inorganic base selected from the group consisting of alkali metal hydroxides and alkali metal carbonates.

7. The method according to claim 6, wherein the molar ratio between said base and menadione 1 is between 0.2:1 and 1.7:1.

8. The method according to claim 6, wherein said inorganic base is sodium hydroxide.

9. The method according to claim 1, wherein said acidification b) is carried out in the presence of a strong acid selected from the group consisting of hydrochloric acid and sulphuric acid.

10. The method according to claim 1, wherein the molar ratio between said acid and hydroxynaphthoquinone 3 is between 2:1 and 10:1.

11. The method according to claim 1, wherein the molar ratio between the chloride of 4-aminobenzoyl and hydroxynaphthoquinone 3 is between 0.8:1 and 2:1.

12. The method according to claim 1, wherein said esterification c) takes place in a nonpolar organic solvent selected from the group consisting of aromatic hydrocarbons, chlorinated solvents, ether solvents, and a mixture thereof.

13. The method according to claim 12, wherein said nonpolar organic solvent is tetrahydrofuran.

14. The method according to claim 1, wherein said reducing agent in step d) is a sulphite.

15. The method according to claim 14, wherein the molar ratio between said reducing agent and compound 4 is between 5:1 and 30:1.

16. The method according to claim 14, wherein said sulphite is sodium hydrosulphite.

17. The method according to claim 1, wherein said reduction d) occurs at a temperature between room temperature and 100° C.

* * * * *